US00RE35699E

United States Patent [19]

Lange et al.

[11] E Patent Number: Re. 35,699

[45] Reissued Date of Patent: Dec. 23, 1997

[54] PROCESS TO CORRECT AND OPTIMIZE THE COMPOSITION OF FEED

[75] Inventors: Stefan Lange, Gothenburg; Ivar Lonnroth, Molndal; Kjell Martinsson, Hassleholm; Leif Goransson, Kagerod, all of Sweden

[73] Assignee: Svenska Lantmannens Riksforbund UPA, Stockholm, Sweden

[21] Appl. No.: 556,239

[22] PCT Filed: Jan. 3, 1991

[86] PCT No.: PCT/SE91/00003

§ 371 Date: Aug. 13, 1992

§ 102(e) Date: Aug. 13, 1992

[87] PCT Pub. No.: WO91/09536

PCT Pub. Date: Jul. 11, 1991

Related U.S. Patent Documents

Reissue of:

[64] Patent No.: 5,296,243
Issued: Mar. 22, 1994
Appl. No.: 854,632
Filed: Jan. 3, 1991

[30] Foreign Application Priority Data

Jan. 4, 1990 [SE] Sweden ..... 9000028

[51] Int. Cl.[6] ..... A23K 1/00

[52] U.S. Cl. ..... 426/2; 426/231; 426/623; 426/630; 426/636; 426/658; 426/656; 426/807

[58] Field of Search ..... 426/231, 2, 623, 426/630, 636, 658, 656, 807

[56] References Cited

U.S. PATENT DOCUMENTS

| | | | |
|---|---|---|---|
| 4,615,891 | 10/1986 | Nocek et al. | 426/231 |
| 4,778,680 | 10/1988 | Hidaka et al. | 426/2 |
| 4,788,065 | 11/1988 | Nakamura et al. | 426/2 |
| 4,981,697 | 1/1991 | Miller et al. | 426/2 |
| 5,008,248 | 4/1991 | Bywater et al. | 426/2 |
| 5,122,512 | 6/1992 | Schrieker | 426/2 |
| 5,158,791 | 10/1992 | Nocek et al. | 426/231 |

OTHER PUBLICATIONS

Krieger D.T., Martin J.B. N. Engl. J. Med. 304:876–855, 1981.

Miller, J. Regulatory Peptides 4 (Suppl): 203–208, 1985.

Lange S., Lonnroth I, FEMS Microbiol. Letters 24:165–168, 1984.

Lonnroth I, Lange S. Biochim. Biophys Acta 883:138–144, 1986.

Lange S., Lonnroth I, Skadhauge E. Pflugers Arch 409:328–332, 1987.

Lonnroth I, Martinsson K. Lange S. J. Vet Med B35:628–635, 1988.

Lonnroth I, Lange S. "Social Strett in Pigs", summary of symposium.

*Primary Examiner*—Esther Kepplinger
*Assistant Examiner*—Choon P. Koh
*Attorney, Agent, or Firm*—Lowe, Price, LeBlanc & Becker

[57] ABSTRACT

The subject of the invention is a process to correct and optimize the feed-composition on basis of testing the levels of so called FIL-lectines in the blood. This correction is exerted by adding certain sugars and amino acids to the feed. Hereby the FIL-level may be adjusted in order to optimize the growth.

11 Claims, No Drawings

PROCESS TO CORRECT AND OPTIMIZE THE COMPOSITION OF FEED

Matter enclosed in heavy brackets [ ] appears in the original patent but forms no part of this reissue specification; matter printed in italics indicates the additions made by reissue.

The daily growth of an animal is to a large degree dependent upon the way in which the nutrients are absorbed in the gut. The absorption of many nutrients such as monosaccharides and amino acids are coupled to the transport/flux of fluid and electrolytes across the intestinal wall. The ability of the body to regulate the flux of fluid and electrolytes across the intestinal mucosa is therefore essential for the daily growth.

During recent years important findings concerning the ability of the body to regulate the exchange of fluid and electrolytes in the gut have been made. Various peptides with the capacity to enhance the resorption of fluid and electrolytes across the intestinal wall have been identified. The most important of these hormone-like peptides are somatostatin, neuropeptide Y (ref. 1, 2) and the so called antisecretory proteins, ASP (3, 4). ASP reverses the secretion and increases the resorption of fluid and electrolytes in the gut; it is the hitherto most potent substance in this respect in rat and pig (4, 5); the molecular weight is about 60000 dalton and the protein chain contains unique antigenic determinants (4). The effect of ASP is determined in rat in a so called intestinal loop test; a section (loop) of the small intestine is ligated by means of a suture; in the loop a certain amount of cholera toxin (usually $3\times10^{-6}$ g) concomitantly with a test substance (antisecretory substance) or a buffer (placebo) is injected intravenously. As a result of the toxic action fluid is secreted into the intestinal loop after a few hours. The antisecrertory effect of the substance, expressed in units, is calculated from the ratio of the weight and the length of the affected loop (mg/cm) in control and test animals (1 unit=the amount of antisecretory substance giving a 50% inhibition of the fluid secretion in the intestinal loop; see reference 3 and 4).

Studies on pigs have revealed that ASP is formed spontaneously and secreted into colostrum and breast milk; during the suckling ASP seems to be transferred to the new-born piglet (6), and a high concentration of ASP in the milk protects the offspring against neonatal diarrhoea.

Surprisingly, it has now been found that the addition to the feed of certain sugars and amino acids induces formation of ASP-like lectines as well as an increase of the daily growth of the animal. The induced proteins and the naturally appearing ASP-protein have the same molecular weights and exert similar intestinal effects, but they differ in their antigenic (antibody-binding) characteristics and their isoelectric point; furthermore they differ in their capacity to be attached to certain polysaccharides such as agarose; like other lectines they are able to elute from the polysaccharide by use of monosaccharides such as α-methyl-D-glucoside or galactose. We will therefore subsequently name these new proteins which are induced by sugars or amino acids "feed-induced lectins" (FIL). The sugars used are mono- or disaccharides or sugar alcohols. The amino acids used are alfa-amino acids. In certain cases the amino acids might be replaced or complemented by amides.

As mentioned above, according to the process of the invention, the sugars used are mono- or disaccharides or sugar alcohols. The preferred sugars are glucose, saccharose and sorbitol. Other sugars which may be used are fructose, galactose, mannose, lactose, mannitol and xylitol.

As mentioned above the amino acids used are alfa-amino acids. The preferred amino acids are tryptophan, aspartic acid lysine, threonine, and methionine. Other amino acids which may be used include glycine, alanine, serine, proline, phenyl alanine, tyrosine, arginine, histidine and glutamic acid. As mentioned above the amino acids in certain cases may be replaced or supplemented by amides. The preferred amide is urea.

Thus, the subject of the invention is a process to correct the composition of the feed leading to the induction of formation of FIL. Like vaccination the process is founded on the induction of synthesis of specific vertebrate proteins. In contrast to the vaccines which consist of antigens of high molecular weight, the amino acids and sugars are, however, of low molecular weight. Further, the induced lectines have quite different characteristics than the antibodies and the lymphokines which are induced by vaccines. One do not know of any similar mechanisms whereby induction of the production of new hormone-like substances may be achieved. Thus, the food-induced lectines seem to be unique in their capacity to be induced by external stimuli. Furthermore, it has surprisingly been found that the production of the new lectines are dose-dependant, i.e. the production increases in proportion to increasing concentrations of free sugars and amino acids in the feed.

By using specific antisera we are able to distinguish between the naturally occurring ASP and the food-induced lectines. As described more in detail in examples 1, 4 and 9, FIL is purified from blood of swine and chicken, respectively, which have been given special feed, whereafter the purified lectines are injected into rabbits in order to get an antiserum (rabbit-anti-pig-FIL and rabbit-anti-chicken-FIL, respectively). We have also prepared antisera against ASP from pig and chicken (antiserum against ASP neutralizes ASP but not FIL). With these different antibodies we are able to neutralize and differentiate the activity of ASP from that of FIL by means of the intestinal loop test described above. By using this bioassay on rat the number of ASP and FIL units in blood or breast milk are determined.

Due to the surprising findings mentioned above the prospect of optimising the content of free sugars and amino acids in the feed for maximum induction of FIL now is opening up by analysing the lectines in the blood or milk of the animals. Feed in this particular context refers to feed, feed-supplements and drink to animals.

The biological effects of FIL are to a great extend the same as those of naturally formed ASP. Like ASP, FIL protects against fluid secretion caused by enterotoxins. Furthermore, it has surprisingly been found that an optimal FIL level in the blood leads to an increased growth. Optimisation of the FIL level might be achieved directly by addition to the feed of the growing animal, or indirectly by addition to the feed of the mother-animal giving breast milk to its growing offspring. The growth-promoting effect of the latter process depends on the finding that FIL like ASP may be transferred via breast-milk and thus exert an effect on the offspring (Example 6).

The most pronounced effect is achieved after the weaning of the pig. The weaning period is critical for the development of the pig and the animal then often become retarded in its growth; the increased sensitivity during this period might be caused by the fact that the increased stress switches off the formation of ASP so that the blood level of ASP drasticly decreases (7). The formation of the food-induced lectines seems to be less sensitive to stress than the natural formation of ASP. By optimising feed for FIL formation, the protection can therefore be maintained also during periods of stress, as during the week after weaning. The practical importance for the breeding farmer is therefore significant.

The invention is further illustrated in the following Examples.

EXAMPLE 1

FIL was extracted from blood by using the affinity of the lectine to agarose gel. To one liter of FIL-containing whole blood (containing anticoagulanting substances) 1 g of sodium thiosulfate and 1 mg of phenylmethylsulfonylfluoride were added. The blood cells were separated by centrifugation and the clear plasma was eluted through a column with Sepharose 6B (Pharmacia LKB Biotechnology, Stockholm), the gel volume corresponded to about 10% of the volume of the solution. After washing with three bed volumes of phosphate buffered physiological saline (PBS= 0.15M Nacl, 0.05M sodium phosphate, pH 7.2), the column was eluted with two bed volumes of 1M α-methyl-D-glucoside dissolved in PBS. The eluate was concentrated on an Amicon PM 10 ultrafilter membrane and was subsequently fractionated by isoelectric focusing according to a previously described technique (4). By means of intestinal loop test in rat the activities and pH of the various fractions were determined. In this way the isoelectric point of the active substance. (=FIL) was obtained. Fractions with high antisecretory activity were pooled, concentrated on Amicon PM10 to 5–8 ml, divided in portions of 1 ml and froozen at −20° C. These fractions were used for molecular weight determination with sodium dodecylsulfate (SDS) polyacrylamide electrophoresis (4), and for immunisation of rabbits to produce antibodies. Antiserum against FIL from pig was adsorbed with ASP from pig: the antibodies were eluted through an agarose column which had been saturated with ASP from pig.

Table I shows how the different species of FIL and ASP were neutralised after they had been mixed with antisera (the ratio antigen/antiserum=1/100) against these antigenes (ASP and FIL respectively) (pFIL=FIL from pig, cASP=ASP from chicken bASP=bovine ASP etc). The FIL-inducing feed compositions are given in examples 4, 8 and 11. ASP from the respective animal species was produced as previously described (4). Table II shows isoelectric point (pI) and molecular weight (=mole.wt) in kilodalton (kDa) of FIL from different animal species. The isoelectric points of ASP from pig, chicken and cattle is 4.7, 4.8 and 4.8, respectively.

TABLE I

Neutralisation of ASP and FIL with antiserum of various origin.

| Antigen | Antiserum produced in rabbits against: pASP | pFIL* | cASP | bASP |
|---|---|---|---|---|
| | (neutralisation +, no neutralisation −) | | | |
| pig ASP | + | − | + | + |
| pig FIL | − | + | − | − |
| chicken ASP | + | − | + | + |
| chicken FIL | − | − | − | − |
| bovine ASP | + | − | (+)** | + |
| bovine FIL | − | N.D.*** | − | − |

*From antiserum against FIL cross-reacting antibodies against ASP were removed by eluting through a column with agarose-bound ASP.
**Partial neutralisation.
***N.D. = not determined.

TABLE II

Characteristics of FIL from various animal species.

| Animal species | pI | mol. wt. (kDa) |
|---|---|---|
| Pig | 4.5 | 92 |
| Chicken | 4.5 | 63 |
| Calf | 4.3 | 92 |

EXAMPLE 2

This example shows the levels of ASP in pigs fed on Swedish standard feed.

TABLE III

The concentration of ASP in blood plasma from pigs with and without diarrhoea (standard feed).

| | Number (n) | ASP-level, units/ml (mean ± SEM) | (range) |
|---|---|---|---|
| Without diarrhoea | 15 | 0.87 ± 0.08 | 0.46–1.42 |
| With diarrhoea | 15 | 0.22 ± 0.05 | 0.01–0.55 |

Blood samples were taken seven days after weaning; the investigation was performed in a herd with approximately 1400 sows and where some 500 pigs were being weaned each week. These pigs were moved at the time of weaning to a weaning unit where the investigation was performed.

From seven days of age the piglets had free access to their own feed. This so called standard feed for piglets had the following composition:

| | |
|---|---|
| Grain | 88% |
| Trace elements, vitamins, minerals | 6.1% |
| Protein feedstuff | 5.8% |
| (addition of free amino acids: lysine 0.39%, methionine 0.03% & threonine 0.1%) | |

TABLE IV

Levels of ASP in relation to number of days after weaning

| Days after weaning | ASP (units/ml blood plasma) (mean ± SEM) | range | significance |
|---|---|---|---|
| 0 | 0.76 ± 0.11 | 0.27–1.41 | |
| 3 | 0.50 ± 0.10 | 0.11–1.04 | $p < 0.1$ |
| 6 | 0.49 ± 0.06 | 0.17–0.70 | $p < 0.1$ |
| 12 | 0.76 ± 0.07 | 0.27–0.89 | N.S. |

(N.S. = no significance)

Table IV shows trio content of ASP in blood plasma in a litter of ten pigs at various times after weaning. The pigs were moved in connection with the weaning to a weaning unit. The study was performed in the same herd and with the same feed as in Table III.

EXAMPLE 3

FIL was induced in pigs by means of solutions containing glucose various amino acids or urea. The results in Example 1 demonstrate that FIL differs from ASP by its biochemical and immunological characteristics; however, both exert similar inhibitory effects on intestinal secretion in the rat intestinal loop test.

TABLE V

| Solution | FIL, units/ml plasma |
|---|---|
| Water | <0.05 |
| 18% glucose | 0.78 |
| 18% glucose + 0.3% tryptophan | 1.02 |
| 12% glucose + 0.3% tryptophan | 0.24 |
| 18% glucose + 0.2% tryptophan | 0.90 |
| 18% glucose + 0.6% glutamic acid | 0.22 |
| 18% glucose + 0.6% arginine | 0.74 |
| 18% glucose + 0.6% glycine | 0.22 |
| 18% glucose + 0.6% aspartic acid | 1.12 |
| 18% glucose + 0.3% aspartic acid + 0.15% tryptophan | 1.56 |
| 18% glucose + 0.3% tryptophan + 1.8% lysine | 1.24 |
| 18% glucose + 0.3% urea | 1.00 |

In this example the Fil-inducing substances were given in a solution to piglets, 4–5 weeks old (about 4 days before weaning). Four piglets per group received 25 ml solution orally twice with an interval of 16 hours; after additionally 5 hours blood-samples for FIL assay were drawn. The pigs also received free amino acids from the standard feed (see Example 2).

EXAMPLE 4

The results of "split-litter"-experiments with piglets receiving ordinary standard feed or FIL-stimulating feed from three weeks of age; the plasma levels of ASP as well as FIL were assayed just before or four days after weaning. The weight and feed consumption of the piglets were registered. Weaning occurred at five weeks of age.

TABLE VI

| | Day 0 | | Day 4 | |
|---|---|---|---|---|
| Feed | ASP | FIL units/ml | ASP | FIL units/ml |
| Control | 0.52 ± 0.06 | <0.05 | 0.38 ± 0.12 | <0.05 |
| Test | 0.24 ± 0.10 | 0.74 ± 0.22 | 0.12 ± 0.22 | 0.56 ± 0.20 |

| Group | Number | Growth gain g/day | Feed conversion kg/kg | Diarrhea frequency % |
|---|---|---|---|---|
| Control | 27 | 266 | 1.98 | 15 |
| Test | 27 | 325 | 1.98 | 4 |

The growth was calculated from the difference in weight between the day before weaning and 28 days after weaning. The control group received standard feed (see Example 2), the test group received in addition to the standard feed also 3% glucose and 0.1% tryptophan in order to stimulate the formation of FIL.

The invention is working also in older pigs as appearent from examples 5 and 6.

EXAMPLE 5

TABLE VII

Induction of FIL in pigs after transfer to a fattening unit.

| Time after movement | Numer of animals | FIL units/ml |
|---|---|---|
| 2 weeks | 4 | <0.05 |
| 3 weeks | 4 | 0.60 ± 0.02 |

The test was performed 2–3 weeks after that the pigs had been moved into the fattening unit; the animals were then 14–15 weeks old. Blood samples were obtained just before and 7 days after provision of the FIL-inducing feed. This feed consisted of:

| | |
|---|---|
| Grain | 85% |
| Glucose | 4.0% |
| Protein feedstuff | 6.2% |
| added amino acids: | |
| lysine 0.34%, threonine 0.11%, aspartic acid 0.10%. | |
| tryptophan 0.05%, methionine 0.03% | |
| Minerals, vitamins, trace elements | 3.3% |
| Fat | 1.5% |

EXAMPLE 6

Transfer of FIl to new-born piglets after stimulation of FIL formation of sows which had received FIL-inducing feed. The levels of FIL in colostrum and in the blood of the piglets were assayed. The standard feed contained the amino acids lysine 0.09% and methionine 0.02%.

TABLE VIII

| | Test | Control |
|---|---|---|
| Number of liters | 5 | 5 |
| Number of piglets | 52 | 52 |
| Diarrhea, % 1–7 days of age | 19 | 35 |
| Level of FIL, units/ml | | |
| Piglets, blood at day 2 | 0.8 | <0.1 |
| Colostrium, day 2 | 0.7 | <0.1 |

TABLE IX

| | Test | Control |
|---|---|---|
| Number of sows | 6 | 6 |
| Level of FIL, units/ml | | |
| Colostrum, day 2 | 0.8 | <0.1 |

Tables VIII and IX show the content of FIL (mean) in colostrum 2 days after deliver. Table VIII also shows the FIL level in blood plasma of 2 days old piglets. The sows in the test group received a supplement of 3% sorbitol (Table VIII) or 3% sucrose plus 0.7% lysine (Table IX) from 7 days before until 6 days after the delivery; the piglets received colostrum only. The sows in the control group received a standard feed consisting of:

| | |
|---|---|
| Grain | 83.6% |
| Minerals, trace elements, vitamins | 3.1% |

-continued

| | |
|---|---|
| Protein feedstuff (added: lysine 0.09%, methionine 0.02%) | 13.3% |

Also in birds the fluid secretion in the gut is regulated by ASP and FIL as demonstrated in examples 7–9.

EXAMPLE 7

TABLE X

Concentration of ASP in eggs and in chicken fed with standard feed.

| | Number of eggs | ASP in eggs (units/ml) |
|---|---|---|
| Egg yolk | 10 | 1.25 |
| Egg white | 10 | 0.28 |
| **Days after hatching** | **Number of animals** | **ASP i plasma (units/ml)** |
| 1 | 10 | 1.03 |
| 7 | 8 | 0.42 |
| 21 | 8 | 0.18 |
| 35 | 8 | 0.91 |

The table reveals that the content of ASP in the chicken blood is decreasing continuously until about three weeks of age when the animals are in their most sensitive state in receiving microbial diseases. In this herb the level of ASP in plasma rised again to near that of the time of birth. The standard feed consisted of:

| | |
|---|---|
| Grain | 76.3% |
| Trace elements, vitamins, minerals | 2.7% |
| Protein feedstuff (added lysine 0.25%, methionine 0.17%) | 21.0% |

TABLE XI

The concentration of ASP in chicken with and without diarrhea.

| | ASP (units/ml) | |
|---|---|---|
| | Test 1 | Test 2 |
| Diarrhea | 0.15 | 0.08 |
| No diarrhea | 0.65 | 0.72 |

Table XI shows the ASP level in plasma from 35 days old chickens with and without diarrhea at slaughter. The chickens were fed by standard feed; the blood samples from 10 chickens were pooled within each group; two experiments were performed and a total of 40 chickens were used.

EXAMPLE 8

Concentration of FIL from chicken fed with FIL-inducing feed.

TABLE XII

| | | FIL (units/ml) Age | |
|---|---|---|---|
| Group | Number | 21 days | 35 days |
| Control | 6 | <0.1 | <0.1 |
| Test | 6 | 1.1 | 1.8 |

The chickens in the test group received a standard feed supplemented with 3% glucose and 0.1% tryptophan.

EXAMPLE 9

Stimulation of FIL-formation and daily growth in chicken.

TABLE XIII

| | Group | | | |
|---|---|---|---|---|
| | I | II | III | IV |
| FIL (units/ml) | 0.1 | 0.2 | 1.5 | 0.7 |
| Weight (kg) | 1.65 | 1.71 | 1.74 | 1.74 |
| Feed gain (kg feed/kg b. wt.) | 1.81 | 1.76 | 1.71 | 1.74 |
| Foot injury | 71% | 25% | 0% | 5% |
| Mortality | 3.9% | 4.0% | 2.9% | 3.9% |

All groups were given the same basic feed from day 0 to day 36 consisting of grain 76%; trace elements, vitamines, minerals 1.7%, protein feed stuff 22% (added tysine 0.05%, methionine 0.11%).

Group I received the basic feed with no addition until the day of slaughter (day 36).

Group II received the basic feed plus 0.07% monensin (coccidiostatic drug) between day 0–32.

Group III received the basic feed plus 1% glucose and 0.02% tryptophan (no monensin) day 0–32.

Group IV: received the basic feed plus 0.07% monensin and 1% glucose between day 0–32.

From day 33 to the slaughter (day 36) all groups received the basic feed without any addition.

The living weight and feed gain (kg feed/leg body weight) was estimated day 36; the FIL value (units/ml blood) was estimated day 35.

The levels of spontaneously occuring ASP and feed-induced FIL was also estimated in calves, which is demonstrated in the following examples:

EXAMPLE 10

ASP-levels in calves fed with standard feed.

TABLE XIV

| Group | Numbers | ASP, units/ml plasma |
|---|---|---|
| Control | 3 | 1.23 ± 0.10 |
| Diarrhoea | 3 | 0.19 ± 0.11 |

The calves were 5–7 weeks old; the reception of milk was 4 L/day and of feed 0.5 kg/day. The feed consisted of: corn 83–89%, protein feedstuff 10–15% and minerals, vitamins and trace elements 1–2%.

EXAMPLE 11

Induction of FIL in calves by addition of sugar and amino acids to the milk.

TABLE XV

| Number (N) | Additions to the milk replacer (g/day) | FIL (units/ml) | Growth gain (g/day) |
|---|---|---|---|
| 14 | 36 g dried whey powder (28 g lactose) | 1.7 | 575 ± 57 |
| 14 | 35 g glucose<br>0.62 g tryptophan<br>0.62 g aspartic acid | 5.5 | 655 ± 90 |

The age of the calves and the feed intake was the same as in the previous example. The daily intake of milk replacers was 200 g; to this amount the stimulators of FIL-formation 36 g of whey powder (group one) or glucose, 35 g, tryptophan, 0.62 g, aspartic acid, 0.62 g (group two) was added, whereafter the mixture was dissolved in two liters of water. The daily weight gain was registred between day 0–18 and the FIL value registred at day 18.

From the example referred it is clear that it is possible to induce the formation of FIL and significantly improve the health and growth gain of animals. The aim of the examples is to show that the effect may be achieved by various means and constitute no limitation of the invention, but shows that an intervall exist in which a maximal effect is achieved. Due to the differences in feed consumtion as well as in sensitivity to FIL-induction, the species and amounts of additions differs between different ages and between different animal species. It is obvious that the effective substances may be added as a premix in the entire ration/fare, as a portion of the total ration/fare or as a separate addition to the ration/fare in the state of a powder or a solution.

We claim:

1. A process to correct and optimize the composition of a feed in order to increase the daily growth of animals which comprises including in the animal's feed a sufficient quantity of at least one material selected from the group consisting of sugars, sugar alcohols, amino acids and amides so that 1.0 ml of that animal's blood will contain at least 0.5 units of lectines, which in a [0.05M]*0.15M* sodium chloride and [0.15M] *0.05M* sodium phosphate buffer and at a pH of 7 will attach with high affinity to agarose and which will dissociate from the agarose after the addition of 1 M-α-methyl-D-glucoside.

2. A process according to claim 1 which comprises daily feeding the animal a feed composition which will provide the animal per kilogram of body weight with 0.1–6 grains of at least one material selected from the group consisting of monosaccharides, disaccharides and sugar alcohols as well as 0.01–5 grams of at least one material selected from the group consisting of free amino acids and amides.

3. A process according to claim 1 which comprises daily feeding a pig, chicken or calf a feed composition which will provide the animal per kilogram of body weight with 0.3–4.0 grams of at least one material selected from the group consisting of monosaccharides, disaccharides and sugar alcohols as well as 0.01–1 gram of at least one material selected from the group consisting of free amino acids and amides.

4. A process according to claim 1 which comprises daily feeding a growing pig a feed composition which will provide the animal per kilogram of body weight with 0.8–2.0 grams of at least one material selected from the group consisting of monosaccharides, disaccharides and sugar alcohols as well as 0.02–0.4 grams of at least one material selected from the group consisting of amino acids and urea.

5. A process according to claim 1 which comprises daily feeding a growing pig a feed composition which will provide the animal per kilogram of body weight with 1.4–1.8 grams of glucose as well as 0.02–0.4 grams of at least one material selected from the group consisting of aspartic acid, lysine, methionine and tryptophan.

6. A process according to claim 1 which comprises daily feeding a sow a feed composition which will provide the animal per kilogram of body weight with 0.5–2.0 grams of at least one material selected from the group consisting of monosaccharides, disaccharides and sugar alcohols as well as 0.01–0.2 grams of at least one material selected from the group consisting of free amino acids and urea.

7. A process according to claim 1 which comprises daily feeding a sow a feed composition which will provide the animal per kilogram of body weight with 0.7–1.2 grams of at least one material selected from the group consisting of sorbitol and saccharose as well as 0.01–0.06 grams of lysine and/or 0.002–0.02 grams of methionine.

8. A process according to claim 1 which comprises daily feeding a chicken a feed composition which will provide the animal per kilogram of body weight with 0.3–4.0 grams of at least one material selected from the group consisting of monosaccharides, disaccharides and sugar alcohols as well as 0.01–1 gram of at least one material selected from the group consisting of free amino acids and urea.

9. A process according to claim 1 which comprises daily feeding a chicken a feed composition which will provide the animal per kilogram of body weight with 0.5–3 grams of glucose as well as 0.01–0.05 grams of tryptophan.

10. A process according to claim 1 which comprises daily feeding a calf a feed composition which will provide the animal per kilogram of body weight with 0.1–2.0 grams of at least one material selected from the group consisting of monosaccharides, disaccharides and sugar alcohols as well as 0.01–0.2 grams of free amino acids.

11. A process according to claim 1 which comprises daily feeding a calf a feed composition which will provide the animal per kilogram of body weight with 0.3–0.8 grams of glucose as well as 0.01–0.2 grams of free amino acids.

* * * * *